United States Patent [19]

Snitman

[11] Patent Number: 4,762,779

[45] Date of Patent: Aug. 9, 1988

[54] COMPOSITIONS AND METHODS FOR FUNCTIONALIZING NUCLEIC ACIDS

[75] Inventor: David L. Snitman, Boulder, Colo.

[73] Assignee: Amgen Inc., Thousand Oaks, Calif.

[21] Appl. No.: 744,508

[22] Filed: Jun. 13, 1985

[51] Int. Cl.[4] .................. C12Q 1/68; C12P 19/34; C07H 15/12
[52] U.S. Cl. ............................. 435/6; 435/91; 536/27; 536/28; 536/29
[58] Field of Search ............... 435/6, 91; 536/27, 28, 536/29

[56] References Cited

FOREIGN PATENT DOCUMENTS 063879 11/1982 European Pat. Off.
0119448 9/1984 European Pat. Off.
2153356A 6/1985 United Kingdom.

OTHER PUBLICATIONS

Beaucage, S. L. et al., Tetrahedron Letters, 22: No. 20, 1859-1862, (1981).
Chu, B. C. F. et al., Nucl. Acid Res., 11, No. 18, 6513-6529, (1983).
Barker et al., J. Biol. Chem., 22, 7135-7147, (1972).
Bauman et al., Histochem. Cytochem., 29, 227-237, (1981).
Broker et al., Nucleic Acids Res., 5, 363-384, (1978).
Chollet et al., Nucleic Acids Res., 13, 1529-1541, (1985).
Cuatrecasas, J. Biol. Chem., 245(12), 3059-3065, (1970).
Kempe et al., Nucleic Acids Res., 13, 45-57, (1985).
McBride et al., Tetrahedron Letters, 24, 245, (1983).
Maniatis et al., Cell, 15, 687, (1978).
Manning et al., Chromosoma (Berl.), 53, 107-117, (1975).
Richards et al., Proc. Natl. Acad. Sci. (U.S.A.), 76, 676-680, (1979).
Watson et al., Science, 218, 381-384, (1982).

Primary Examiner—Sidney Marantz
Assistant Examiner—Jack Spiegel
Attorney, Agent, or Firm—Marshall O'Toole

[57] ABSTRACT

A composition and a method for 5'-labelling polynucleotides undergoing solid phase synthesis wherein a phosphoramidite of an ω-hydroxylamine is condensed to a support-bound polynucleotide.

4 Claims, No Drawings

COMPOSITIONS AND METHODS FOR FUNCTIONALIZING NUCLEIC ACIDS

BACKGROUND

The present invention pertains in general to compositions and methods for functionalizing nucleic acids and in particular to compositions and methods for the 5' labelling of polynucleotides attached to a support.

Attachment of a detectable label to a polynucleotide permits detection and quantitation of a nucleic acid. The attachment of detectable labels to nucleic acids is particularly important in hybridization assays wherein a labelled polynucleotide probe is used to search a sample for a target nucleic acid which has a complementary nucleotide sequence and which has been immobilized by hybridization to a support-bound polynucleotide probe. Labelling with a reactive group permits attachment of reporter groups to or immobilization of the polynucleotide.

One approach to labelling a polynucleotide probe for use in hybridization assays involves binding a radioisotope (e.g., $^{32}P$, $^{3}H$, or $^{125}I$) to the probe. However, difficulties inherent in the two methods of detecting radioactive labels limit the usefulness of the technique. Autoradiography is a time-consuming procedure which relies upon reduction of silver ions to form silver grains in a photographic emulsion; and scintillation counting, the other detection technique, requires expensive equipment and a certain amount of delay as well. Furthermore, radioisotopes require special handling for safety reasons. Some radioactive isotopes, such as $^{125}I$, have relatively short shelf-lives, which further limit their usefulness in a clinical diagnostic setting.

In non-radioactive labelling systems, a probe is "labelled" with a reporter group which is associated with a signal to enable detection. A reporter is an agent which is used to associate a signal with a probe for indicating the presence or location of the probe. The signal itself, which is directly perceptible, may be generated by a separate or separable signal molecule. A label is properly a type of reporter which incorporates a signal.

One approach to the attachment of labels to probes is described in Ward, et al., European patent application No. 63,879. Ward discloses the preparation of probes having a biotin reporter molecule covalently attached to a purine or pyrimidine ring. Selected biotinylated purines and pyrimidines are then directly incorporated within the phosphodiester backbone of the nucleic acid of the probe by enzymatic means. However, enzymatic techniques are costly and difficult to perform.

Other approaches link a label to a probe by way of a protein. Single-stranded polio virus RNA is naturally linked to a protein which may be reacted with the N-hydroxysuccinimidyl ester of biotin to obtain an RNA probe having a biotinylated reporter group detectable by specific attachment of avidincoated spheres. Richards, et al., *Proc.Natl.Acad.Sci. (USA)*, 76: 676–680 (1979). Similarly, biotin-labelled cytochrome c may be coupled to RNA by reaction in the presence of formaldehyde and thereafter labelled with avidin-coated spheres. Manning, et al., *Chromosoma (Berl.)*, 53: 107–117 (1975). Nevertheless, because not all nucleic acids desired to be labelled are naturally associated with proteins and because the location and amount of cytochrome c binding to a nucleic acid is not readily predictable, it is desirable to have a chemical synthetic technique for end-labelling.

In one such chemical synthetic technique, nucleic acids are converted to 3'-aldehydes by oxidation and condensed with alkyldiamines or polyamines to provide a reporter group for the attachment of biotin. Broker, et al., *Nucleic Acids Res.*, 5: 363–384 (1978). Similarly, aldehydes generated by the periodate oxidation of nucleic acids may be used to couple fluorescent labels to the nucleic acids. Bauman, et al., *J. Histochem.Cytochem.*, 29: 227–237 (1981). However, it is desirable to have a technique for attaching reporter groups to polynucleotides attached to a support in an automated process for nucleic acid synthesis.

In yet another approach to 5' labelling, biotin is converted to 2-(biotinylamido)ethanol and condensed to a phosphorylated, polymer-supported nucleotide. The condensation of the aminoethanol derivative of biotin to the 5' hydroxyl group of a ribose ring gives a stable phosphodiester bond upon deprotection of the nucleotide. Kempe, et al., *Nucleic Acids Res.*, 13: 45–57 (1985). Nevertheless, specific reporter groups are attached by this approach so that the approach does not permit preparation of an oligonucleotide with a reactive functionality which may later be used to attach a variety of desired reporter groups.

Nucleotides in solution have been amine-functionalized by condensation with protected 6-amino-1-hexanol phosphate. Barker, et al., *J.Biol.Chem.*, 22: 7135–7147 (1972). However, these procedures are difficult to perform and have not been integrated with solid-phase synthesis.

In another approach to binding nucleotides to supports, in the purification of nucleases by affinity chromatography, single nucleotides, 3'-derivatized with p-aminophenol are attached to a gel matrix by a linker. The linker is formed by attaching 3,3' diaminodipropylamine to the matrix using cyanogen bromide and azide. The resulting amine-functionalized gel is treated with succinic anhydride and then coupled to the amine-functionalized nucleotide. Cuatrecasas, *J.Biol.Chem.*, 12: 3059–3065 (1978). Nevertheless, the manufacture of the amine-functionalized nucleotide itself has been performed in solution by tedious procedures. See, e.g., Barker, et al., *J.Biol.Chem.*, 22: 7135–7147 (1972).

In an approach to 5' labelling, a 5-aminoalkyl phosphoramidate derivative of a kinased, unprotected oligonucleotide is prepared in solution. Kination of a deprotected oligonucleotide is accomplished by T4 polynucleotide kinase. The kinased oligonucleotide is reacted with an imidazole and a diamino alkane. The resulting 5'-aminoalkyl phosphoramidite DNA is reacted with biotin-N-hydroxysuccinimidyl ester in potassium N,N-dimethylformamide to produce a biotin-labelled oligodeoxyribonucleotide. Chollet, et al., *Nucleic Acids Res.*, 13: 1529–1541 (1985). Although this method makes use of an oligonucleotide synthesized using the solid-phase phosphoramidite method or the solid-phase phosphotriester method, the oligonucleotide is deprotected, detached from the solid phase, isolated, and purified before functionalization. After functionalization, a second isolation and purification is required. Because each isolation and purification entails losses and is time-consuming, it is desirable to functionalize a polynucleotide during solid-phase synthesis. Furthermore, the kination reaction suffers from the problems of cost and difficulty generally associated with enzymatic procedures.

Therefore, there is a need for a method and composition for the generic attachment of reporter groups to polynucleotides undergoing solid phase synthesis.

SUMMARY OF THE INVENTION

A composition according to the present invention involves an end-label for attachment to a nucleic acid during solid phase synthesis. The end-label is a phosphoramidite of a hydroxylamine.

A method according to the present invention involves attaching an end-label to a nucleic acid during solid phase synthesis. Specifically, a phosphoramidite of a hydroxylamine is condensed to a support-bound deoxyoligonucleoside.

DETAILED DESCRIPTION

According to the present invention, a phosphoramidite of a hydroxylamine, preferably an ω-hydroxylamine, is condensed to a oligonucleoside bound to a support. The support may be of any sort useful for the solid phase synthesis of nucleic acids, including, but not limited to, silicates and cellulose. The polynucleoside may be a ribonucleoside or a deoxyribonucleoside.

An ω-hydroxylamine according to the present invention may generally be of any length, but is preferably from two to ten carbons in length. The ω-hydroxylamine may be alkyl, aryl, cycloalkyl, or generally of any structure which permits condensation of the hydroxyl moiety to an oligonucleoside and also permits reaction of the amine moiety with a reporter group without steric hindrance. Specifically, preferred ω-hydroxylamines include ethanolamine, propanolamine, butanolamine, pentanolamine, hexanolamine, heptanolamine, octanolamine, nonanolamine, decanolamine, and p-aminophenol.

Reporter groups for use with the present invention include biotinyl, N-hydroxysuccinimide, and fluorescein isothiocyanate. A particular advantage of the present invention over methods wherein a reporter group is directly attached to the synthetic oligonucleotide, is that labels or reporter groups are not required to withstand the harsh conditions required to deprotect a synthetic polynucleotide. Thus, by the method according to the present invention, an oligonucleotide may be 5' labelled with biotin, hapten, antigen, and fluorescent or chemiluminescent functionalities, among others.

For use in the hybridization procedures of the following examples, a single-stranded phage containing either the (+) plus (coding) strand or the (−) minus (anticoding) strand of the Herpes Simplex Virus Type I (HSV-I) Glycoprotein D (gD) gene was employed as the target sequence. A portion of the double-stranded gene sequence is set out in Table I below, the bottom strand being the anticoding strand. This sequence has been published in Watson, et al., Science, 218: 381–384 (1982). Portions of the plus strand have been employed as probes according to the present invention. These single-stranded probe sequences have been designated on Table I by a lettered line drawn above the coding strand of the gene.

TABLE I

```
         10              20              30              40
GTG GCC CCG GCC CCC AAC AAA AAT CAC GGT AGC CCG GCC GTG
TAC CGG GGC CGG GGG TTG TTT TTA GTG CCA TCG GGC CGG CAC 50              60              70              80
TGA CAC TAT CGT CCA TAC CGA CCA CAC CGA CGA ACC CCT AAG
ACT GTG ATA GCA GGT ATG GCT GGT GTG GCT GCT TGG GGA TTC 90             100             110             120
GGG GAG GGG CCA TTT TAC GAG GAG GAG GGG TAT AAC AAA GTC
CCC CTC CCC GGT AAA ATG CTC CTC CTC CCC ATA TTG TTT CAG 130             140             150             160
TGT CTT TAA AAA GCA GGG GTT AGG GAG TTG TTC GGT CAT AAG
ACA GAA ATT TTT CGT CCC CAA TCC CTC AAC AAG CCA GTA TTC 170             180             190             200             210
CTT CAG CGC GAA CGA CCA ACT ACC CCG ATC ATC AGT TAT CCT
GAA GTC GCG CTT GCT GGT TGA TGG GGC TAG TAG TCA ATA GGA 220             230             240             250
TAA GGT CTC TTT TGT GTG GTG CGT TCC GGT ATG GGG GGG ACT
ATT CCA GAG AAA ACA CAC CAC GCA AGG CCA TAC CCC CCC TGA 260             270             280             290
GCC GCC AGG TTG GGG GCC GTG ATT TTG TTT GTC GTC ATA GTG
CGG CGG TCC AAC CCC CGG CAC TAA AAC AAA CAG CAG TAT CAC 300             310              320            330
                              A
GGC CTC CAT GGG GTC CGC GGC AAA TAT GCC TTG GCG GAT GCC
CCG GAG GTA CCC CAG GCG CCG TTT ATA CGG AAC CGC CTA CGG 340             350             360             370
TCT CTC AAG ATG GCC GAC CCC AAT CGC TTT CGC GGC AAA GAC
AGA GAG TTC TAC CGG CTG GGG TTA GCG AAA GCG CCG TTT CTG
```

TABLE I-continued

```
       380         390         400         410         420
   CTT CCG GTC CTG GAC CAG CTG ACC GAC CCT CCG GGG GTC CGG
   GAA GGC CAG GAC CTG GTC GAC TGG CTG GGA GGC CCC CAG GCC 430         440         450         460
   CGC GTG TAC CAC ATC CAG GCG GGC CTA CCG GAC CCG TTC CAG
   GCG CAC ATG GTG TAG GTC CGC CCG GAT GGC CTG GGC AAG GTC 470         480         490         500
   CCC CCC AGC CTC CCG ATC ACG GTT TAC TAC GCC GTG TTG GAG
   GGG GGG TCG GAG GGC TAG TGC CAA ATG ATG CGG CAC AAC CTC 510         520         530         540
   CGC GCC TGC CGC AGC GTG CTC CTA AAC GCA CCG TCG GAG GCC
   GCG CGG ACG GCG TCG CAC GAG GAT TTG CGT GGC AGC CTC CGG 550         560         570         580
   CCC CAG ATT GTC CGC GGG GCC TCC GAA GAC GTC CGG AAA CAA
   GGG GTC TAA CAG GCG CCC CGG AGG CTT CTG CAG GCC TTT GTT 590         600         610         620         630
   CCC TAC AAC CTG ACC ATC GCT TGG TTT CGG ATG GGA GGC AAC
   GGG ATG TTG GAC TGG TAG CGA ACC AAA GCC TAC CCT CCG TTG 640         650         660         670
   TGT GCT ATC CCC ATC ACG GTC ATG GAG TAC ACC GAA TGC TCC
   ACA CGA TAG GGG TAG TGC CAG TAC CTC ATG TGG CTT ACG AGG

G  680         690         700         710
   TAC AAC AAG TCT CTG GGG GCC TGT CCC ATC CGA ACG CAG CCC
   ATG TTG TTC AGA GAC CCC CGG ACA GGG TAG GCT TGC GTC GGG 720         730         740         750
   CGC TGG AAC TAC TAT GAC AGC TTC AGC GCC GTC AGC GAG GAT
   GCG ACC TTG ATG ATA CTG TCG AAG TCG CGG CAG TCG CTC CTA 760         770         780         790
   AAC CTG GGG TTC CTG ATG CAC GCC CCC GCG TTT GAG ACC GCC
   TTG GAC CCC AAG GAC TAC GTG CGG GGG CGC AAA CTC TGG CGG 800         810         820         830         840
   GGC ACG TAC CTG CGG CTC GTG AAG ATA AAC GAC TGG ACG GAG
   CCG TGC ATG GAC GCC GAG CAC TTC TAT TTG CTG ACC TGC CTC 850         860         870         880
   ATT ACA CAG TTT ATC CTG GAG CAC CGA GCC AAG GGC TCC TGT
   TAA TGT GTC AAA TAG GAC CTC GTG GCT CGG TTC CCG AGG ACA 890         900         910         920
   AAG TAC GCC CTC CCG CTG CGC ATC CCC CCG TCA GCC TGC CTC
   TTC ATG CGG GAG GGC GAC GCG TAG GGG GGC AGT CGG ACG GAG 930         940         950         960
   TCC CCC CAG GCC TAC CAG CAG GGG GTG ACG GTG GAC AGC ATC
   AGG GGG GTC CGG ATG GTC GTC CCC CAC TGC CAC CTG TCG TAG 970         980         990        1000
   GGG ATG CTG CCC CGC TTC ATC CCC GAG AAC CAG CGC ACC GTC
   CCC TAC GAC GGG GCG AAG TAG GGG CTC TTG GTC GCG TGG CAG 1010        1020        1030        1040        1050
   GCC GTA TAC AGC TTG AAG ATC GCC GGG TGG CAC GGG CCC AAG
   CGG CAT ATG TCG AAC TTC TAG CGG CCC ACC GTG CCC GGG TTC 1060        1070        1080        1090
   GCC CCA TAC ACG AGC ACC CTG CTG CCC CCG GAG CTG TCC GAG
   CGG GGT ATG TGC TCG TGG GAC GAC GGG GGC CTC GAC AGG CTC
```

TABLE I-continued

```
         1100          1110          1120          1130
ACC CCC AAC GCC ACG CAG CCA GAA CTC GCC CCG GAA GAC CCC
TGG GGG TTG CGG TGC GTC GGT CTT GAG CGG GGC CTT CTG GGG 1140          1150          1160          1170
GAG GAT TCG GCC CTC TTG GAG GAC CCC GTG GGG ACG GTG GCG
CTC CTA AGC CGG GAG AAC CTC CTG GGG CAC CCC TGC CAC CGC 1180          1190          1200          1210
CCG CAA ATC CCA CCA AAC TGG CAC ATC CCG TCG ATC CAG GAC
GGC GTT TAG GGT GGT TTG ACC GTG TAG GGC AGC TAG GTC CTG 1220          1230          1240          1250          1260
GCC GCG ACG CCT TAC CAT CCC CCG GCC ACC CCG AAC AAC ATG
CGG CGC TGC GGA ATG GTA GGG GGC CGG TGG GGC TTG TTG TAC 1270          1280          1290          1300
        GGC CTG ATC GCC GGC GCG GTG GGC GGC AGT CTC CTG GCA GCC
        CCG GAC TAG CGG CCG CGC CAC CCG CCG TCA GAG GAC CGT CGG 1310          1320          1330          1340
CTG GTC ATT TGC GGA ATT GTG TAC TGG ATG CAC CGC CGC ACT
GAC CAG TAA ACG CCT TAA CAC ATG ACC TAC GTG GCG GCG TGA 1350          1360          1370          1380
CGG AAA GCC CCA AAG CGC ATA CGC CTC CCC CAC ATC CGG GAA
GCC TTT CGG GGT TTC GCG TAT GCG GAG GGG GTG TAG GCC CTT 1390          1400          1410          1420
GAC GAC CAG CCG TCC TCG CAC CAG CCC TTG TTT TAC TAG ATA
CTG CTG GTC GGC AGG AGC GTG GTC GGG AAC AAA ATG ATC TAT 1430          1440          1450          1460          1470
CCC CCC CTT AAT GGG TGC GGG GGG GTC AGG TCT GCG GGG TTG
GGG GGG GAA TTA CCC ACG CCC CCC CAG TCC AGA CGC CCC AAC 1480          1490          1500          1510
GGA TGG GAC CTT AAC TCC ATA TAA AGC GAG TCT GGA AGG GGG
CCT ACC CTG GAA TTG AGG TAT ATT TCG CTC AGA CCT TCC CCC 1520          1530          1540          1550
GAA AGG CGG ACA GTC GAT AAG TCG GTA GCG GGG GAC GCG CAC
CTT TCC GCC TGT CAG CTA TTC AGC CAT CGC CCC TGC GCG GTG 1560          1570          1580          1590
CTG TTC CGC CTG TCG CAC CCA CAG CTT TTT CGC GAA CCG TCC
GAC AAG GCG GAC AGC GTG GGT GTC GAA AAA GCG CTT GGC AGG

1600
CGT TTT CGG GAT
GCA AAA GCC CTA
```

The target used in the examples is a single-stranded phage, phage 2 (Φ2), which contains 1,454 bases of the HSV-I glycoprotein D (gD) gene (i.e., bases 67 through 1,287, initiation codon nucleotide number 241 cloned into a plasmid, M13mp18. The minus strand sequence of gD in Φ2 is employed as a target complementary to the (+) plus strand probes identified above.

The following examples describe a series of experiments demonstrating various aspects of the present invention.

Example 1 shows the effectiveness of labelling of an antibody-coated polynucleotides according to the present invention. Example 2 illustrates the use of a probe labelled according to the present invention for capturing a hybridization sandwich comprising two probes bound to a target.

EXAMPLE 1

A polynucleotide having the sequence

5'-P-ACC GAA TGC TCC TAC AAC AAG TCT C-3' was labelled with an antigen at its 5' end employing the method according to the present invention.

Specifically, a first probe was oligonucleotide G as described above. Such 5' labelling of oligonucleotide G may be accomplished with fluorescein.

Oligonucleotide G was 5' fluorescein labelled by reacting a 5' amine functionalized oligonucleotide G with fluorescein isothiocyanate. The 5' amine functionalized oligonucleotide G was formed by reacting oligonucleotide G bound by its 3' end to a solid support with a phosphoramidite having the general formula [(CH$_3$)$_2$CH ]$_2$NP(OCH$_3$)O(CH$_2$)$_8$NH(DMT) wherein DMT is a dimethoxytrityl group.

In the synthesis of this phosphoramidite, about 8 ml of diazomethane-ether solution were added to 159.2 mg (1 mmole) of ω-aminocaprylic acid (available from Aldrich Chemical, Milwalkee, Wisconsin) in 10 ml of methanol. The methanol was evaporated to yield 174.9 mg of m-aminocaprylic acid methyl ester. Next, 173 mg (1 mmole) of the ω-aminocaprylic acid methyl ester, 1 mmole of dimethoxytrityl chloride, and 1 mmole of diisopropylethyl amine were added to 5 ml of anhydrous tetrahydrofuran under an argon atmosphere at 0° C. This mixture was warmed to 25° C. and stirred for 1 hour. The solvent was evaporated and the crude product was diluted with 50 ml of ethyl acetate and washed successively with two portions of water, saturated bicarbonate, and brine. The product was dried over anhydrous magnesium sulfate and evaporated to yield 460 mg of a dimethoxytrityl derivative of the ω-aminocaprylic acid methyl ester (ACAM-DMT). To 0.17 mmoles of ACAM-DMT in 1 ml of anhydrous tetrahydrofuran under an argon atmosphere at −78° C. was added 1.24 ml of 1 molar lithium aluminum hydride in tetrahydrofuran. This reaction mixture was stirred for 5 minutes at −78° C. and was then stirred for 30 minutes at 25° C. before being diluted with 10 ml of 5% H2O in tetrahydrofuran, 200 ml of ether, 3 g of cellite, and 0.5 g of anhydrous magnesium sulfate. The resulting mixture was stirred for 30 minutes and filtered to yield an alcohol having the general formula HO(CH$_2$)$_8$NH-DMT.

To 0.72 mmoles of HO(CH$_2$)$_8$NH-DMT in 10 ml of anhydrous dichloromethane was added 0.76 mmoles of diisopropyl ethyl amine and 0.76 mmoles of chloro-N,N'-diisopropylaminomethoxy phosphene (as available from American Bionuclear, Emeryville, California). This mixture was stirred for 40 minutes at 25° C., and then diluted with 50 ml of ethyl acetate and washed with four portions of brine. The product of this reaction was coupled to a support-bound deoxynucleoside G employing the phosphoramidite synthesis technique for use with deoxynucleoside N,N-diisopropyl amino methoxyphosphines in polymer support deoxyoligonucleotide synthesis according to McBride, et al., *Tetrahedron Letters*, 24: 245 (1983).

Quantitation of binding of the reporter group according to the present invention to the deoxyoligonucleoside was determined by a demethoxytrityl assay as follows:

$$\text{Percent coupling} = \frac{A_{498} \times \text{dilution}}{\mu\text{moles label applied}} \times 14.3 \times 10^2$$

wherein A$_{498}$ is the absorbence of the solution containing the removed demethoxytrityl components measured at a wavelength of 498 nm. Coupling was determined to be in excess of 90% by this method.

EXAMPLE 2

A second probe, oligonucleotide A, was labelled with $^{32}$P according to the procedure of Maniatis, et al., *Cell*, 15: 687 (1978). The specific activity of the probe on the date of use was 3.2×10$^6$ cpm/picomole.

Oligonucleotide G without a 5' fluorescein label was used as a first probe control. A second control probe, having the sequence 5' CATGATCTTGCGGTC-GGATTCTTC 3', which does not complement any of the target sequence, was also $^{32}$P-labelled and had a specific activity on the date of use of 3.2×10$^6$ cpm/picomole.

The target used was single-stranded Φ2. Singlestranded Φ2 is complementary to the first and second probes and to the first probe control, but not to the second control probe.

As a support, one-quarter-inch polystyrene beads of the sort available from Pierce Chemical, Rockland, Illinois, were coated with fluorescein antibody (anti-fluorescein). Anti-fluorescein production was induced in rabbits. The antifluorescein was purified by ammonium sulfate precipitation, followed by DEAE cellulose chromatography. In solution, the anti-fluorescein had an affinity of approximately 10$^{12}$ and quenched the fluorescence of fluorescein by about 99%.

To prepare an anti-fluorescein-coated bead, the bead is cleaned by ultrasonication for 15 seconds in 10 mM NaHCO$_3$ buffer at pH 8. After ultrasonication, the beads are washed in deionized water until all fines are removed. Approximately 200 heads are covered by 40 ml of 10 mM NaHCO$_3$. Next, 7 ml of purified anti-fluorescein at a concentration of 0.57 mg/ml is added. The beads are incubated for approximately 65 hours at room temperature. After incubation, the beads are washed with deionized water and air-dried on a suction filter.

Each of the anti-fluorescein coated beads is capable of binding greater than 1.4 picomole of fluorescein, as demonstrated by incubation of single beads with 1.5 ml of 1 nM fluorescein in TDX buffer (0.1 M NaPO$_4$, pH 7.5; 0.1% NaN$_3$; 0.1% bovine gammaglobulin). During 20 hours of incubation at 25° C., 97% of the fluorescein was removed from solution. After washing the beads three times in 5 ml of deionized water and blotting the beads dry after each wash, the beads were incubated in 0.1 M NaOH for 10 minutes, in which 60% of the originally applied amount of fluorescein was released into solution. Thus, each bead has approximately 0.9 picomole of fluorescein binding capacity.

(1) A series of capture experiments employing 5'-fluorescein-labelled oligonucleotides, 5'-biotin-labelled oligonucleotides (both 3'-$^{32}$P end-labelled), and kinased $^{32}$P-labelled oligonucleotides and polystyrene beads coated with anti-fluorescein were run under the following conditions.

With 200 µg/ml denatured sheared salmon sperm DNA (Sigma Chemical Company, St. Louis, Missouri) containing 1 picomole of one of the $^{32}$P-labelled oligonucleotides, 100 µl of TDX buffer (0.1 M sodium phosphate, pH 75; 0.1% NaN$_3$; and 0.01% bovine gamma globulin, Sigma Chemical Company, St. Louis, Missouri) was mixed. An anti-fluorescein-coated polystyrene bead was added to this solution. After incubating this system for 18 hours at 25° C., the bead was removed and washed for 5 minutes in 1 ml of TDX buffer at 25° C. The bead was then counted in a scintillation counter.

The stability of the antibody complex on the bead was tested by washing the bead for 5 minutes at increasing temperatures. The capture efficiency and stability of a series of such beads is shown in Table II.

TABLE II

| Temperature | Percent cpm Capture Complexes | | |
|---|---|---|---|
| | 5' fluorescein-labelled complex | 5' biotin-labelled complex | 5' $^{32}$P-labelled complex |
| 25 | 63 | 4 | 3 |
| 35 | 61 | 1 | 0 |
| 45 | 56 | 0 | 0 |
| 55 | 51 | 0 | 0 |
| 65 | 42 | 0 | 0 |
| 75 | 35 | 0 | 0 |
| 85 | 20 | 0 | 0 |
| 95 | 0 | 0 | 0 |

As illustrated by Table II, these beads have a high capture efficiency and stability of the sort which is useful in a hybridization capture system. Because little or no biotin or $^{32}$P-labelled oligonucleotide binds to these beads, indicating little non-specific binding to the beads, the background in such a system is very low.

(2) In order to more precisely determine the rate of capture of a fluorescein-labelled oligonucleotide by a fluorescein antibody-coated bead, each of a series of beads was incubated for a different amount of time with 1 picomole of 5'-fluorescein-labelled oligonucleotide A which had been 3' end-labelled with $^{32}$P. The percent of capture was determined for each bead and the results are shown below in Table III.

TABLE III

| Time | Percent Oligonucleotide Capture |
|---|---|
| 0 | 0 |
| 15 minutes | 20 |
| 30 minutes | 45 |
| 1 hour | 48 |
| 2 hours | 75 |
| 3 hours | 91 |
| 4 hours | 90 |
| 5 hours | 88 |
| 6 hours | 86 |
| 7 hours | 85 |
| 8 hours | 82 |
| . | |
| . | |
| . | |
| 20 hours | 68 |

As illustrated in Table III, 90% of the 5' fluorescein-labelled oligonucleotide is captured by the bead in 2 to 3 hours. The slow decline in the amount of radiolabel over time on the bead most likely represents a small amount of leakage of the antibody from the bead.

(3) Experiment 1. The capture-efficiency of the anti-fluorescein-coated beads being established, 1 picomole of the first probe (5'-fluorescein-labelled oligonucleotide G), 1 picomole of the second probe ($^{32}$P-labelled oligonucleotide A), specific activity on date of use $3.2 \times 10^6$ cpm/picomole), and 1 picomole of the target (Φ2 SS, complementary to both the first and second probes) were diluted to 50 μl with 5×SSPE diluted from 20×SSPE (3.6 M NaCl; 0.23 M NaH$_2$PO$_4$, pH 7.5; and 20 mM EDTA). This hybridization solution was incubated for 3 hours at 50° C. This hybridization solution was diluted with 100 μl of TDX buffer and one anti-fluorescein-coated bead was added. After incubation for 3 hours at 25° C., the bead was washed with 1 ml of TDX buffer for 5 minutes at 37° C. and was re- washed with 1 ml of TDX buffer for 5 minutes at 37° C. before counting in a scintillation counter.

Control Experiments. Three control experiments were run according to the same protocol but with the following modifications. In a first control experiment (Control 1), 5' fluorescein-labelled oligonucleotide G, as a first probe, and 5' $^{32}$P-labelled oligonucleotide A, as a second probe, were incubated with the anti-fluorescein-coated bead in the absence of any target. A second control experiment (Control 2) involved the use of 1 picomole of unlabelled oligonucleotide G as a first probe for the fluorescein-labelled oligonucleotide G of experiment 1. Finally, a third control experiment (Control 3) was performed with 1 picomole of 5'-fluorescein-labelled oligonucleotide G, as a first probe, 1 picomole of a $^{32}$P-labelled oligonucleotide designated 32-B$_2$ (the sequence of which is complementary to Φ2 SS), as a second probe, and 1 picomole of Φ2 SS as a target.

The results of these experiments are summarized in Table IV.

TABLE IV

| Experiment | % $^{32}$P Oligonucleotide Bound to the Bead |
|---|---|
| Experiment | 4.2 |
| Control 1 | 0.002 |
| Control 2 | 0.07 |
| Control 3 | 0.22 |

A comparison of Experiment and Control 1 indicates that the hybrid comprising fluorescein-labelled oligonucleotide G, Φ2 SS, and $^{32}$P-labelled oligonucleotide A may be selectively captured by an anti-fluorescein-coated solid support. Controls 2 and 3 demonstrate that in the absence of the correct antigenlabelled first probe or in the absence of the correct target complementary second probe, a hybrid is not effectively generated or captured.

It is expected that numerous modifications and variations will occur to those skilled in the art upon consideration of the present invention. For example, although ω-hydroxylamines are exemplified herein, any molecule having hydroxyl and amine groups available for respectively forming a bond with a support-bound nucleoside and a reporter group may be employed. Consequently, it is intended that the present invention be given the full scope of the appended claims.

What is claimed is:

1. An end-label for attachment to a nucleic acid during solid phase synthesis comprising a phosphoramidite of a hydroxylamine condensed to a polynucleoside.

2. The label according to claim 1 wherein said hydroxylamine contains from 1 to 10 carbon atoms.

3. The label according to claim 2 wherein said hydroxylamine is selected from the group comprising ethanolamine, propanolamine, butanolamine, pentanolamine, hexanolamine, heptanolamine, octanolamine, nonanolamine, decanolamine, and p-aminophenol.

4. A method of attaching an end-label to a nucleic acid during solid phase synthesis comprising the steps of:

preparing a phosphoramidite of a hydroxylamine; and
condensing the phosphoramidite of a hydroxylamine to a support-bound polynucleoside.

* * * * *